United States Patent
Sezeur et al.

(10) Patent No.: US 8,418,545 B2
(45) Date of Patent: Apr. 16, 2013

(54) GAS INSUFFLATION DEVICE PROVIDING OPTIMAL AND SAFE USE OF PRESSURED GAS VESSELS

(75) Inventors: Alain Sezeur, Cachan (FR); Fabien Dromigny, Nezignan l'Eveque (FR); Jean-Rémi Sandraz, La Ciotat (FR); Améziane Aoussat, Montrouge (FR)

(73) Assignees: Sopro, La Ciotat Cedex (FR); Universite Pierre et Marie Curie-Paris 6'eme, Paris Cedex 06 (FR)

( * ) Notice: Subject to any disclaimer, the term of this patent is extended or adjusted under 35 U.S.C. 154(b) by 720 days.

(21) Appl. No.: 12/312,298

(22) PCT Filed: Nov. 6, 2007

(86) PCT No.: PCT/FR2007/052303
§ 371 (c)(1),
(2), (4) Date: Jan. 22, 2010

(87) PCT Pub. No.: WO2008/056082
PCT Pub. Date: May 15, 2008

(65) Prior Publication Data
US 2010/0130917 A1  May 27, 2010

(30) Foreign Application Priority Data
Nov. 8, 2006 (FR) .................................. 06 54787

(51) Int. Cl.
*G01F 22/02* (2006.01)
(52) U.S. Cl.
USPC ............................................................ 73/149

(58) Field of Classification Search ............... 73/149
See application file for complete search history.

(56) References Cited

U.S. PATENT DOCUMENTS

| 5,299,568 | A |   | 4/1994  | Forare et al. |
|-----------|---|---|---------|---------------|
| 5,383,499 | A |   | 1/1995  | Mattern       |
| 5,423,741 | A |   | 6/1995  | Frank         |
| 5,800,381 | A | * | 9/1998  | Ognier ............................ 604/26 |
| 6,299,592 | B1|   | 10/2001 | Zander        |
| 7,100,800 | B2| * | 9/2006  | Saavedra et al. .................. 222/3 |
| 2005/0222491 | A1 | | 10/2005 | Noda et al.  |
| 2005/0222534 | A1 | | 10/2005 | Uesugi et al. |
| 2006/0129087 | A1 | * | 6/2006 | Uesugi et al. .................... 604/26 |

FOREIGN PATENT DOCUMENTS

| DE | 26 11 698 | 9/1977 |
| JP | 4-176472  | 6/1992 |
| WO | 94/01154  | 1/1994 |

\* cited by examiner

*Primary Examiner* — Hezron E Williams
*Assistant Examiner* — Paul West
(74) *Attorney, Agent, or Firm* — Clark & Brody

(57) ABSTRACT

A medical gas insufflation device comprising at least a gas outlet circuit, a connector for connecting a pressurized vessel in which the gas is packaged, an expander placed between the connector and the gas outlet circuit, a high-pressure sensor placed between the connector and the expander, a flow meter placed at the outlet from the expander, and a microprocessor connected at least to the sensor to receive signals representative of the pressure observed at the connector and to the flow meter to receive signals representative of the flow rate at the outlet from the expander, wherein the microprocessor includes evaluation means for evaluating the remaining volume of gas after expansion as a function of the signals received from the sensor and the flow meter during a gas expansion operation.

16 Claims, 2 Drawing Sheets

GAS INSUFFLATION DEVICE PROVIDING OPTIMAL AND SAFE USE OF PRESSURED GAS VESSELS

BACKGROUND OF THE INVENTION

The present invention relates to the general field of medical gas insufflation devices, in particular those used in surgery. The present invention relates more particularly to monitoring the quantity of gas remaining in a pressurized vessel connected to a passive or active insufflation device, the vessel typically being a cylinder containing gas that may optionally be liquefied.

The purpose of such monitoring is to ensure that the cylinder is changed soon enough to avoid insufflation needing to be interrupted suddenly and in untimely manner while in use.

Such monitoring is thus essential to avoid untimely and harmful stopping of insufflation in the middle of surgery or of therapy. At present, the quantity of gas remaining is conventionally monitored by monitoring the pressure within the cylinder. Warnings are thus issued to indicate that the pressure has dropped below a warning threshold, e.g. 10 bars.

Nevertheless, cylinders of a variety of formats, and thus containing different quantities and kinds of gases for a given internal pressure, can all be connected to the insufflation device.

When using small-capacity cylinders, the warning corresponds approximately to the remaining volume being too small for performing or terminating surgery or therapy.

However with cylinders of greater capacity, cylinder-empty warnings are triggered by a pressure threshold even though there still remains enough gas to continue one or even more surgical interventions or sessions of therapy without risk, even though the generally-low warning pressure has been reached. Frequently, the quantity of gas that is not used could have served to perform one or more other surgical interventions or sessions of therapy. In contrast, with a small cylinder, the warning is given late and leaves little time to change the cylinder before insufflation ceases.

OBJECT AND SUMMARY OF THE INVENTION

A main object of the present invention is thus to mitigate this drawback. The invention relates in particular to monitoring the content of cylinders contained pressurized or even liquefied gas coming to the end of their use, i.e. in particular when all of the gas remaining in the cylinder is in the gas phase.

The invention thus provides a medical gas insufflation device comprising at least a gas outlet circuit, a connector for connecting a pressurized vessel in which the gas is packaged, an expander placed between the connector and the gas outlet circuit, a high-pressure sensor placed between the connector and the expander, a flow meter placed at the outlet from the expander, and a microprocessor connected at least to the sensor to receive signals representative of the pressure observed at the connector and to the flow meter to receive signals representative of the flow rate at the outlet from the expander, wherein the microprocessor includes evaluation means for evaluating the remaining volume of gas after expansion as a function of the signals received from the sensor and the flow meter during a gas expansion operation.

With such a device, evaluating the remaining volume of gas after expansion makes it possible to decide to change the cylinder when the remaining volume of gas is not sufficient to perform a surgical intervention or a session of therapy. The decision whether or not to change the cylinder is no longer taken with reference to a pressure threshold, as has been the case in the past.

In particular, the invention makes it possible to use the gas remaining in a large-capacity cylinder for which the pressure that is observed when there really is not enough gas to perform a surgical intervention or a session of therapy is much lower than the pressure threshold.

Thus, evaluating the remaining volume after expansion is at least an additional safety measure for small cylinders and at best a source of savings.

According to a characteristic of the invention, the evaluation means comprise means for evaluating the remaining volume of gas after expansion as being the ratio of the expanded volume obtained from the flow rate and the duration of the expansion divided by the pressure drop generated by the expansion and measured by the sensor multiplied by the remaining pressure as measured by the sensor, at the end of the expansion operation.

Such a calculation presents the advantage of being simple to implement, even though it includes approximations, in particular concerning the influence of temperature. Nevertheless, this characteristic assumes that the flow meter in which the gas is still at a pressure intermediate between the pressure in the cylinder and atmospheric pressure, measures the volume of gas as expanded to atmospheric pressure. This is generally true of all of the flow meters used in this field. Otherwise, it is necessary to incorporate a simple correction factor into the calculation.

In another particular embodiment of the invention, the evaluation means comprise means for calculating the expanded volume from the observed flow rate and from the duration needed by the expansion operation to cause the pressure to drop by a previously-selected interval.

With such a characteristic, a previously-selected pressure drop is a constant interval over which the expanded volume is calculated. The remaining volume after expansion is then evaluated as a function of this expanded volume measured during the previously-selected pressure drop.

In another particular embodiment of the invention, the evaluation means comprise means for measuring a pressure drop at the end of the operation of expanding a previously-selected expanded volume.

With such a characteristic, the expanded volume is previously selected and it is the pressure drop caused by extracting this expanded volume of gas that enables the remaining volume of gas after expansion to be evaluated.

Thus, when the device is in use, the expanded volume may be calculated or the pressure drop may be measured respectively on each occasion there is a drop by the selected pressure interval or at the end of each successive occasion on which a selected expanded volume has been expanded.

The monitoring performed in accordance with the invention is particularly reliable when the gas is completely in the gas phase, i.e. generally towards the end of the use of a cylinder. However, when at least some of the gas is still in the liquid phase, the remaining quantity of gas in terms of volume is not easily measured. The pressure within the vessel is then highly variable as a function of ambient temperature. The pressure may thus vary over the range 50 bars to 65 bars, at the ambient temperatures generally to be found in operating theaters in temperate regions, i.e. in the range 16° C. to 20° C. Frequently, the quantity of gas in the cylinder is then sufficient, but that is not always so with small cylinders.

In addition, it should be added that the fact of expanding the gas causes it to cool. This has the direct consequence of also causing its pressure to drop. Using the pressure that is then observed at the outlet from the cylinder thus introduces an error when calculating the remaining volume.

The invention also seeks to remedy this problem by proposing a device that includes a temperature probe suitable for measuring the temperature of the gas leaving the cylinder and connected to the microprocessor, the microprocessor being suitable for using this temperature measurement to ensure that the evaluated remaining volume of gas after expansion is reliable.

With such a characteristic, monitoring the remaining volume after expansion remains possible even with small cylinders or with gases that present liquid phases at relatively low pressures.

Advantageously, the device is then such that in the event of a temperature change in excess of a given limit being observed during an expansion operation that is used for evaluating the remaining volume after expansion, the microprocessor triggers an action selected from the following: issuing a warning, not displaying the volume remaining after expansion, and determining a correction factor as a function of the temperature change and using the correction factor when evaluating the volume remaining after expansion.

According to an advantageous characteristic, the evaluation means are arranged in such a manner that they are activated when the sensor measures a pressure below a given threshold.

In the light of the above, and when a temperature probe is not used, such a threshold advantageously corresponds to the pressure at which it is known, for ordinary temperatures, that the gas contained in the vessel is entirely in the gas phase. For example, with carbon dioxide, this pressure is 49 bars.

This avoids using the evaluation means when the gas is still partially liquid in the cylinder and when there are no means for correcting, or at least indicating, temperature variations.

According to a particular characteristic of the invention, when the device is not in use, the evaluation means are arranged in such a manner that they can be activated momentarily by triggering an expansion operation that is predefined by a given pressure drop or by a given volume of expanded gas.

According to an advantageous characteristic, the device includes means for momentarily activating the evaluation means manually or that operate on receiving a signal. The manual activation means are advantageously a button placed on the device so as to be pressed by an operator or a user. The signal received by the signal receiver means may be a signal coming from a remote control or a voice signal.

With such characteristics, it is possible voluntarily to trigger an operation of evaluating the remaining volume while the device is not in use. This is particularly advantageously when the device is switched on, e.g. by an operating theater nurse who can then decide at once whether or not to change the cylinder as a function both of the number of surgical interventions that are to be performed and of the evaluated remaining volume after expansion. The invention thus makes it possible to propose checking the remaining volume after expansion prior to using the device for one or more surgical interventions. This is very useful in operating theaters or in care services, or in home services where decisions generally need to be taken quickly and safely.

The use of a voice control is particularly advantageous when the device is being used for therapy at the home of an invalid patient incapable of pressing the button.

According to a characteristic of the invention, the remaining volume of gas after expansion is displayed on display means connected to the microprocessor.

Such a display is useful for informing the operator of the insufflation device about the quantity of gas that is available, so as to make sure the operator knows immediately and prior to putting the device into use, whether the device can be used in complete safety.

According to an additional characteristic of the device of the invention, the evaluation means enable the type of vessel that is connected thereto to be detected as a function of calculation of the ratio of the expanded volume obtained from the flow rate and the duration of the expansion operation divided by the pressure drop generated by the expansion and measured by the sensor.

Providing the gas contained in the cylinder is in the gas phase, such an additional characteristic is useful for informing the operator, so that the operator can be sure about the capacity of the cylinder that is still available.

Such detection of the type of cylinder that is connected to the device replaces any manual selection, and consequently a potential source of error, of the kind that arises in the prior art for indicating the type of cylinder that is connected.

Advantageously, the type of connected vessel as detected is displayed on the display means.

The invention also provides a method suitable for being implemented in a microprocessor of an insufflation device of the invention to evaluate the remaining volume of gas after expansion that is contained in a vessel connected to the insufflation device, the method comprising the steps of triggering an operation of expanding the gas, receiving signals representative of the pressure within the vessel from the high-pressure sensor, receiving signals representative of the flow rate at the outlet from the expander from the flow meter, and evaluating the remaining volume of gas after expansion as a function of the received signals.

In a preferred implementation, the various steps of the method are determined by computer program instructions.

Consequently, the invention also provides a computer program product on a data medium, the program product being suitable for being implemented in a microprocessor, and including instructions adapted to implement the steps of the method of the invention.

The program may use any programming language, and may be in the form of source code, object code, or code intermediate between source code and object code, such as in a partially compiled form, or in any other desirable form.

The invention also provides a microprocessor-readable data medium that includes computer program instructions as specified above.

The data medium may be any entity or device capable of storing the program.

Alternatively, the data medium may be an integrated circuit in which the program is incorporated, the circuit also being adapted to execute or to be used in the execution of the method in question.

BRIEF DESCRIPTION OF THE DRAWINGS

Other characteristics and advantages of the present invention appear from the following description made with reference to the accompanying drawings that show an embodiment having no limiting character.

In the figures.

DETAILED DESCRIPTION OF AN EMBODIMENT

Figure 1:
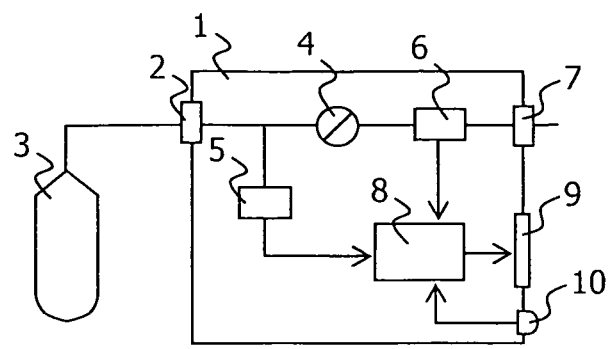
FIG. 1 is a diagram of a medical gas insufflation device of the invention.

FIG. 1 is a diagram of an insufflation device 1 of the invention. Such a device 1 comprises a connector 2 for connecting to a vessel 3 under pressure, generally a cylinder of liquefied gas. As explained above, cylinders of liquefied gas exist in several formats, and the invention serves to optimize use of such cylinders of different formats.

The insufflation device 1 also includes an expander 4 with the gas at the outlet therefrom being at a pressure that is fixed and constant, e.g. 3 bars or 3.5 bars. It also has a high-pressure sensor 5 placed between the connector 2 and the expander 4, and a flow meter 6 placed at the outlet from the expander 4. The expander 4 is connected to a gas outlet circuit 7 that enables insufflation of the gas to be controlled by modulating the pressure at the outlet from the device.

The sensor 5 and the flow meter 6 are connected to a microprocessor 8 that controls display means 9, advantageously implemented directly on a front face of the insufflation device 1.

Figure 2:
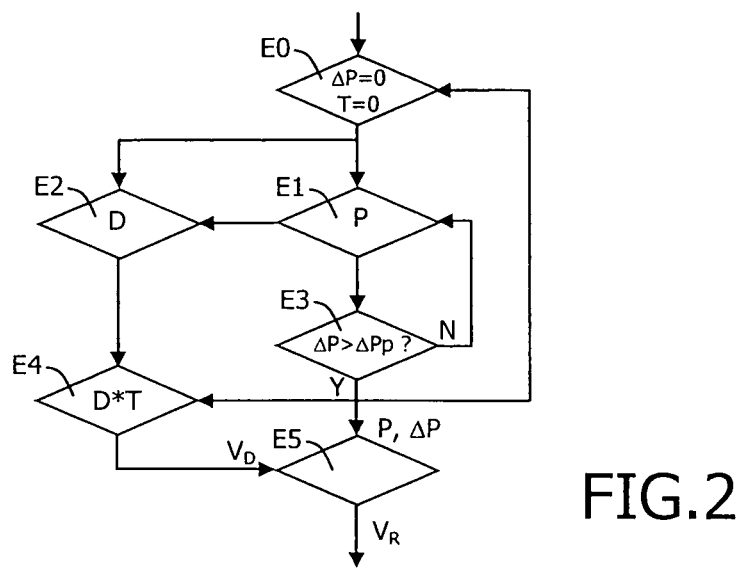
FIG. 2 is a flow chart showing a method of the invention.

The microprocessor 8 implements a method of the invention as shown in FIG. 2. The method may be triggered manually by pressing a button 10 placed on the front face of the insufflation device 1 and connected to the microprocessor, in order to cause the method of the invention to be performed, else the method may be triggered each time an expansion operation is performed while the device 1 is in use. When triggered manually, the microprocessor 8 is advantageously connected to a valve of the outlet circuit 7 for controlling the operation thereof, opening the valve causing the gas to expand and be delivered, and/or connected to a valve situated in the connector 2 or close thereto, likewise for controlling the operation thereof, opening the valve also causing the gas to expand and be delivered through the insufflation device 1.

The method of the invention comprises a step E0 of initialization and triggering an expansion operation. For example, two registers of the microprocessor 8 contain respectively data concerning the pressure drop and data concerning the elapsed duration of an expansion operation, and these two registers are initialized to a value of zero.

As stated above, it is observed that expansion may be triggered either by using the device for insufflation, or by voluntarily triggering the device manually prior to using it, in order to check the quantity of gas remaining.

In both situations, the sensor and the flow meter send signals to the microprocessor, which receives them inparallel in steps E1 and E2 throughout the time that expansion continues. These signals are representative of the pressure P upstream from the expander, and thus the pressure in the cylinder, and of the flow rate D at the outlet from the expander.

In the example proposed below, attention is given to the situation in which expansion is triggered by manual activation of evaluation means, e.g. by pressing the button 10.

By way of example, such an expansion operation may be predefined as being one that delivers a pressure drop ΔPp of 0.1 bars. The magnitude of the pressure drop that is triggered by manually activating the method of the invention is selected both as a function of the quantity of gas that it is acceptable to lose while evaluating the quantity that remains after the expansion operation, and as a function of the sensitivity of the high-pressure sensor.

The received pressure P is used in a step E3 where the predetermined pressure drop ΔPp is detected. In parallel, in a step E4, the expanded volume $V_A$ converted to atmospheric pressure, is calculated by the microprocessor 8 by integrating the flow rate D over the time T that elapses during expansion until the predetermined pressure drop ΔPp of 0.1 bars is observed.

In the example proposed, expansion is continued, as represented diagrammatically by the N arrow looping back to step E1, until the pressure drop ΔP reaches the predetermined pressure drop ΔPp, which corresponds to the Y arrow.

Under such circumstances, both the expansion operation and the step E4 of integrating the flow rate D over the duration T are stopped, and the registers are reinitialized in a new step E0.

Such reinitialization makes it possible to restart evaluating the volume remaining after expansion during a subsequent operation of expanding the gas.

This is particularly useful when the expansion operation is due to the device being used for insufflation, and is therefore continuous. For example, under such circumstances, 0.1 bar increments of pressure drop are used to define intervals at which the remaining volume $V_R$ is evaluated.

Once the integration of the expanded volume $V_A$ converted to atmospheric pressure $P_A$ has stopped, this value $V_A$ is transmitted to a step E5 for evaluating the volume remaining after expansion. This step E5 then calculates the ratio of the expanded volume $V_A$ divided by the pressure drop ΔPp multiplied by the remaining pressure P2 observed by the sensor at the end of the expansion.

This calculation gives directly the value of the volume $V_R$ remaining after expansion by performing the theoretical calculations explained below.

In the vessel under pressure, assuming the gas to be a perfect gas, the gas state equation is PV=nRT, where P is the pressure, V is the volume of the vessel, n is the number of gas molecules, T is the temperature, and R is the perfect gas constant.

During the expansion ΔP of the gas from P1 to P2 within the cylinder, corresponding to n1-n2 molecules leaving the cylinder, it is thus known that $$V\Delta P = V(P1-P2) = (n1-n2)RT$$

Since the flow meter generally measures the flow rate converted to atmospheric pressure $P_A$, the volume after expansion measured with the flow meter being written $V_A$, the following also applies:

$$P_A V_A = (n1-n2)RT$$

where $V_A$ is the volume expanded to atmospheric pressure as measured by the flow meter.

This gives $V = P_A V_A / \Delta P$.

Since $P_A$ is atmospheric pressure, it can be seen that the ratio of the expanded volume $V_A$ divided by the pressure drop ΔP gives an estimate of the volume V of the vessel 3 connected to the device 1.

It is then possible to determine automatically the volume of the cylinder. According to an advantageous characteristic, the invention thus makes it possible to detect the size of the vessel 3 connected thereto. This size is advantageously indicated on the display means 9, an example of which is shown diagrammatically in FIG. 3.

Figure 3:
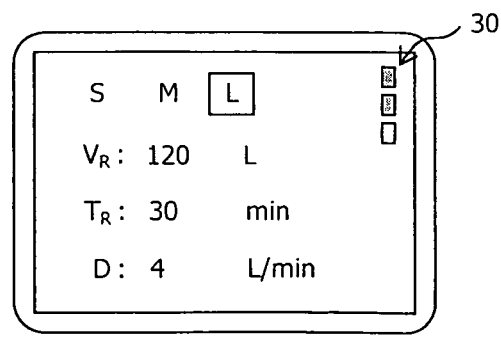
FIG. 3 shows display means in a preferred embodiment of the invention.

FIG. 3 shows an example involving a display screen 9, e.g. an LCD screen, placed on the front face of an insufflation device 1 of the invention.

The type of cylinder is advantageously indicated by highlighting, one of the letters S, M, or L corresponding to different sizes of cylinder and displayed on the screen, e.g. by putting the letter into a box or by making it bold. Once the gas in the cylinder is in the gas phase, one of the advantages of the invention is thus to make it possible to weight alarms as a function of cylinder size, given certain knowledge of cylinder size is available that is derived from physical measurement of the type of cylinder that is connected to the device. For example, the pressure threshold will be lower for cylinders of large capacity than for cylinders of small capacity, which small-capacity cylinders are used at present for determining pressure alarm thresholds.

Alarms may be audible, and they may also be visible, as shown in FIG. 3 by a set 30 of three strips of different colors, e.g. green, orange, and red, or as shown strips that are shaded more darkly going from bottom to top. The green or lightest shade corresponds to pressures greater than 10 bars, the orange or medium shade corresponds to pressures between 10 bars and an alarm pressure threshold that depends on the type of cylinder that has been detected, and the red or darkest shade corresponds to pressures below the alarm pressure threshold that depends on the detected cylinder type.

Thereafter, the volume $V_R$ remaining in the cylinder 3 is calculated by multiplying the previously-estimated volume V of the cylinder by the remaining pressure P2 as observed in the cylinder 3 and measured by the sensor 5, and dividing by a factor specified by the pressure $P_A$, which is the pressure to which the flow rate measured by the flow meter is converted.

This gives $$P2 \cdot V = nRT = P_A V_R$$

where $V_R$ is the volume remaining after expansion. $P_A$ is equal to 1 when the flow meter converts its measurements to atmospheric pressure, as is generally the case. This gives direct access to the remaining volume $V_R$ after expansion by multiplying the previously determined volume V by the pressure P2 observed at the end of the pressure drop ΔP.

The remaining volume $V_R$ after expansion is then also advantageously displayed on the display means 9. Conventionally, the flow rate D is also displayed.

In addition, it is appropriate to provide for another calculation to be performed by the microprocessor 8 in order to estimate the remaining insufflation time $T_R$ on the basis of the flow rate D as observed in real time. To calculate this estimate, it is also possible to make use of an average of the flow rate D over a given lapse of time. In the example described, the flow rate D is 4 liters per minute (L/min) and the evaluated remaining volume $V_R$ is 120 liters (L), so the remaining time $T_R$ is evaluated as being 30 minutes.

The calculations given above give an exact evaluation of the remaining volume after expansion providing all the gas is in the gas phase, or when the gas is partially in the liquid phase but expansion has not given rise to a significant drop in temperature leading to a significant drop of pressure within the vessel.

Otherwise, when the gas is partially in the liquid phase, a temperature drop leads to a pressure drop and that makes the above calculations erroneous since the pressure drop is then no longer due solely to the reduction in the amount of gas inside the vessel.

Figure 4:
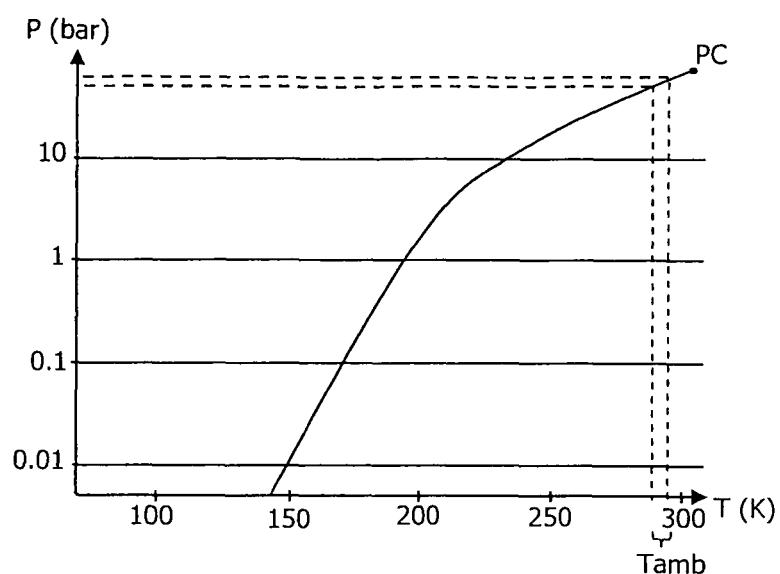
FIG. 4 is a pressure-temperature diagram corresponding to carbon dioxide.

FIG. 4 plots the curve of pressure P, on a logarithmic scale, as a function of temperature T for carbon dioxide up to its critical point PC. It can be seen that at ambient temperatures Tamb in temperate regions, as marked by dashed lines, the slope of the pressure P is not negligible. Thus, the slightest variation in temperature T quickly ceases to be negligible, because of the pressure drop it generates compared with the pressure drop generated by delivering gas.

Since the expansion of gas inevitably leads to the gas cooling, the verification proposed by the invention ceases to be reliable.

Thus, when the device is for operating with cylinders that are liable to contain gas that is still in the liquid phase even at the end of use (as applies with small cylinders), it is appropriate to provide the device 1 with a temperature probe connected to the microprocessor 8.

The microprocessor 8 is then provided with means for handling such data. This may consist in a warning to the effect that given the temperature drop observed during the pressure drop, the displayed remaining volume is necessarily erroneous. When the microprocessor 8 detects a temperature drop of more than 1° C., for example, it may also be arranged that during the following expansion operation used for calculating the remaining volume, said volume is not displayed.

Finally, in a more precise embodiment, the microprocessor then may be suitable for determining a correction factor that is calculated as a function of the temperature changes observed by the temperature probe. This correction factor is then input into the calculation of the remaining volume. It needs to be adapted as a function of the gas in question by referring to the pressure/temperature curve for that gas.

Finally, it should be observed that various implementations can be provided on the principles of the invention as defined by the following claims. In particular, the method of the invention may be implemented as soon as an expansion operation has been performed. The method can thus be performed continuously with the calculation and the display of the remaining volume after expansion being periodically updated, updating advantageously being performed at regular intervals of pressure drop intervals.

It is also possible to make provision for a sound to be emitted when the remaining volume appears to be less than a given value. Such an audible alarm may be implemented on its own or in combination with display means as described above.

What is claimed is:

1. A medical gas insufflation device comprising at least a gas outlet circuit, a connector for connecting a pressurized vessel in which the gas is packaged, an expander placed between the connector and the gas outlet circuit, a high-pressure sensor placed between the connector and the expander, a flow meter placed at the outlet from the expander, and a microprocessor connected at least to the sensor to receive signals representative of the pressure observed at the connector and to the flow meter to receive signals representative of the flow rate at the outlet from the expander, wherein the microprocessor includes evaluation means for evaluating the remaining volume of gas after expansion as a function of the signals received from the sensor and the flow meter during a gas expansion operation, wherein the evaluation means comprise means for evaluating the remaining volume of gas after expansion as being the ratio of the expanded volume obtained from the flow rate and the duration of the expansion divided by the pressure drop generated by the expansion and measured by the sensor, multiplied by the remaining pressure as measured by the sensor at the end of the expansion operation.

2. A device according to claim 1, wherein the evaluation means comprise means for calculating the expanded volume from the observed flow rate and from the duration needed by the expansion operation to cause the pressure to drop by a previously-selected interval.

3. A device according to claim 2, wherein, while the device is in use, the means for calculating the expanded volume or the means for measuring the pressure drop are such that the calculation or the measurements are performed respectively on each occasion the pressure drops by the selected interval or at the end of each successive occasion on which a selected expanded volume has been expanded.

4. A device according to claim 1, wherein the evaluation means comprise means for measuring a pressure drop at the end of the operation of expanding of a previously-selected expanded volume.

5. A device according to claim 1, including a temperature probe suitable for measuring the temperature of the gas leaving the cylinder and connected to the microprocessor, the microprocessor being suitable for using said temperature measurement to ensure the reliability of the evaluated remaining volume of gas after expansion.

6. A device according to claim 5, wherein the microprocessor includes means for triggering an action when a temperature change greater than a given limit is observed during an expansion operation used for evaluating the remaining volume after expansion, the action being selected from the following: issuing a warning, determining a correction factor as a function of the temperature change and using said correction factor when evaluating the volume remaining after expansion.

7. A device according to claim 1, wherein the evaluation means are arranged in such a manner that they are activated when the sensor measures a pressure below a given threshold.

8. A device according to claim 1, wherein when the device is not in use, the evaluation means are arranged in such a manner that they can be activated momentarily by triggering an expansion operation that is predefined by a given pressure drop or by a given volume of expanded gas.

9. A device according to claim 8, including means for momentarily activating the evaluation means manually or that operate on receiving a signal.

10. A device according to claim 9, wherein the manual activation means are constituted by a button placed on the device so as to be pressed by an operator or a user.

11. A device according to claim 9, including means for receiving a signal coming from a remote control or a voice signal.

12. A device according to claim 1, including display means connected to the microprocessor to display the remaining volume of gas after expansion.

13. A device according to claim 1, wherein the evaluation means comprise means enabling the type of vessel connected thereto to be detected as a function of calculation of the ratio of the expanded volume obtained from the flow rate and the duration of the expansion operation divided by the pressure drop caused by the expansion and measured by the sensor.

14. A device according to claim 13, including display means for displaying the detected type of vessel that is connected thereto.

15. A method suitable for being implemented in a microprocessor of an insufflation device according to claim 1, in order to evaluate a remaining volume of gas after expansion during an operation of expanding the gas contained in a vessel connected to the insufflation device, the method comprising the steps of:
triggering an expansion operation;
receiving signals representative of the pressure within the vessel and coming from the high-pressure sensor;
receiving signals representative of the flow rate at the outlet from the expander and coming from the flow meter; and
evaluating the remaining volume of gas after expansion as a function of the received signals.

16. A computer-readable recording medium having a computer program recorded thereon including instructions for executing the steps of the method according to claim 15.

* * * * *

UNITED STATES PATENT AND TRADEMARK OFFICE
CERTIFICATE OF CORRECTION

PATENT NO. : 8,418,545 B2 Page 1 of 1
APPLICATION NO. : 12/312298
DATED : April 16, 2013
INVENTOR(S) : Sezeur et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 978 days.

Signed and Sealed this
First Day of September, 2015

Michelle K. Lee
*Director of the United States Patent and Trademark Office*